US00PP36709P2

(12) United States Plant Patent
Schulze et al.

(10) Patent No.: US PP36,709 P2
(45) Date of Patent: May 27, 2025

(54) ***BUDDLEIA* PLANT NAMED 'Bailbudone'**

(50) Latin Name: *Buddleia davidii*
Varietal Denomination: Bailbudone

(71) Applicant: Bailey Nurseries Inc., Newport, MN (US)

(72) Inventors: Justin Schulze, Athens, GA (US); David Jonathan Roberts, Woodbury, MN (US); Oren McBee, Bishop, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 18/496,846

(22) Filed: Oct. 28, 2023

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
CPC ..... A01H 5/02; A01H 5/00; A01H 6/00
See application file for complete search history.

(56) References Cited

PUBLICATIONS

Plant Haven International, Inc. *Buddleja* Buzz Soft Pink, retrieved on Nov. 19, 2024 at https://planthaven.com/plant/buddleja-buzz-soft-pink/, 3 pp. (Year: 2024).*

* cited by examiner

*Primary Examiner* — June Hwu
(74) *Attorney, Agent, or Firm* — Penny J. Aguirre

(57) ABSTRACT

A new cultivar of *Buddleia* plant named 'Bailbudone' that is characterized by its a compact and uniform growth habit, its flower panicles that are vibrant pink in color, and its upright and rounded plant habit.

2 Drawing Sheets

Botanical classification: *Buddleia davidii.*
Variety denomination: 'Bailbudone'.

BACKGROUND OF THE INVENTION

The present invention relates to a new and distinct cultivar of *Buddleia davidii* and will be referred to hereafter by its cultivar name, 'Bailbudone'. 'Bailbudone' is a new shrub grown for use as an ornamental landscape plant.

The new cultivar was derived from a controlled breeding program conducted by the Inventors in Winterville, Georgia. The goal of the breeding program is to develop new cultivars of butterfly bush with compact plant habits and sterile flowers.

'Bailbudone' originated as a seedling that arose from seed planted from open pollination of *Buddleia* 'Boscranz' (U.S. Plant Pat. No. 25,730) in summer of 2019. The male parent is therefore unknown. 'Bailbudone' was selected as a single unique plant in summer of 2020 from the resulting seedlings.

Asexual propagation of the new cultivar was first accomplished by softwood stem cuttings by one of the Inventors in Winterville, Georgia in summer of 2021. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailbudone' as a unique cultivar of *Buddleia.*

1. 'Bailbudone' exhibits a compact and uniform growth habit.
2. 'Bailbudone' exhibits flower panicles that are vibrant pink in color.
3. 'Bailbudone' exhibits an upright and rounded plant habit.

The female parent differs from 'Bailbudone' in having flowers that are red-purple with orange centers in color and an open (less dense) and arching plant habit. 'Bailbudone' can be compared to the *Buddleia* cultivars 'Tobudsopi' (not patented) and 'Pink Delight' (not patented). 'Tobudsopi' is similar to 'Bailbudone' in having flowers that are pink in color and a compact plant habit. 'Tobudsopi' differs from 'Bailbudone' in having a smaller plant size, flowers that are paler pink in color, and an upright arching plant habit. 'Pink Delight' is similar to 'Bailbudone' in having flowers that are pink in color and a similar plant size. 'Pink Delight' differs from 'Bailbudone' in having flowers that are lighter pink in color and a rounded, arching plant habit.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the filing date. Disclosures include a website listing by Mark-Watch Plants.

BRIEF DESCRIPTION OF THE DRAWINGS

The accompanying photographs illustrate the characteristics of a 3-year-old plant of the new cultivar as grown in a trial garden in Winterville, Georgia.

The photograph in FIG. 1 provides a view of a plant of 'Bailbudone' in bloom.

Figure 1:
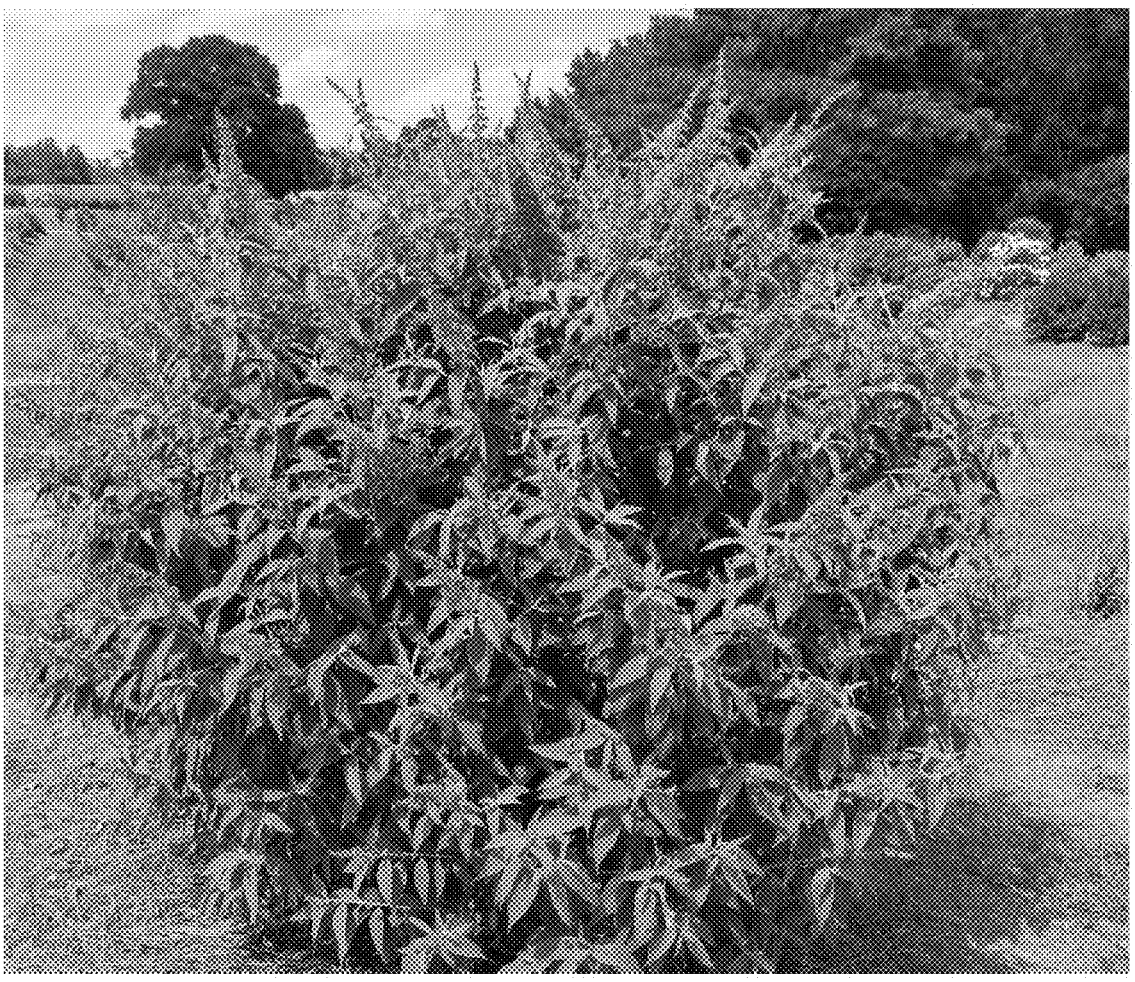
Figure 2:
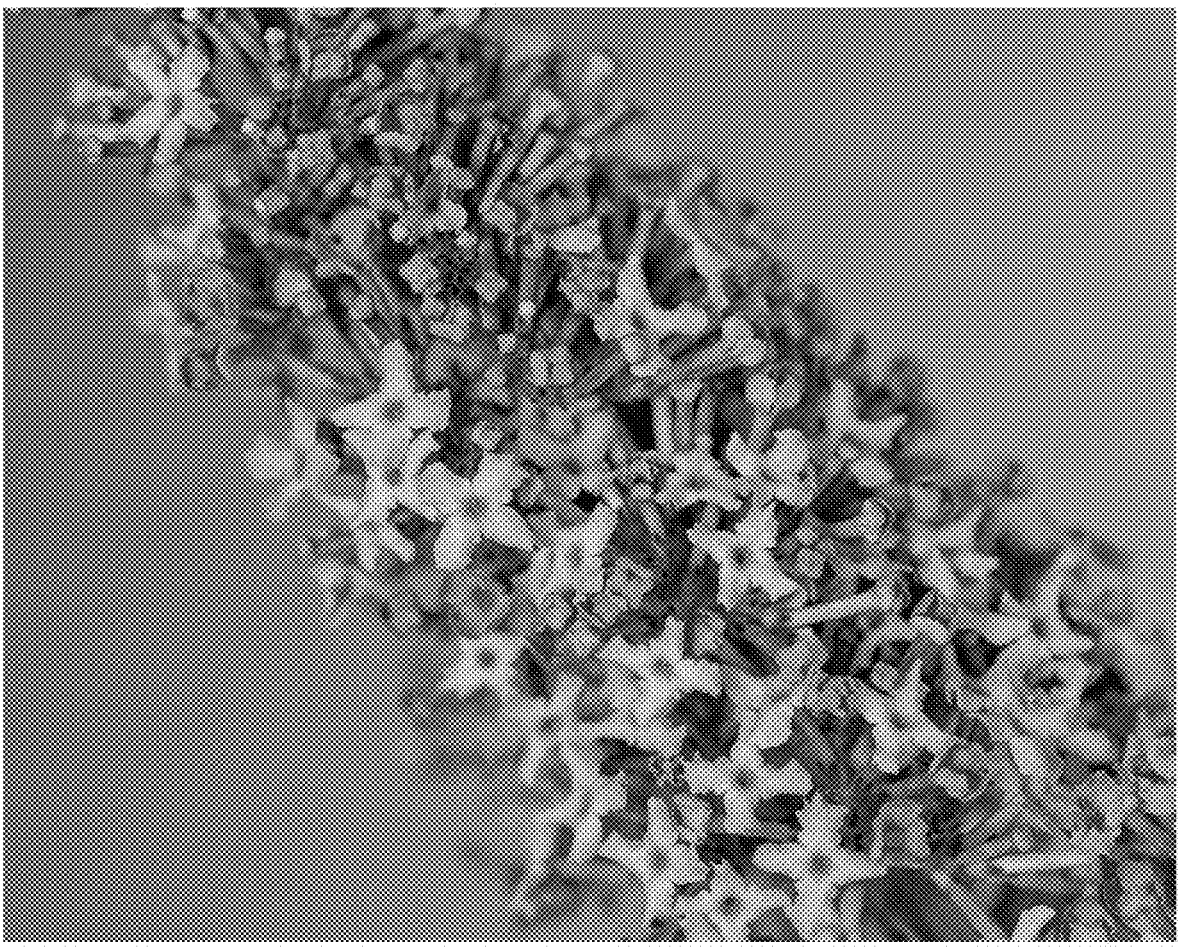

The photograph in FIG. 2 provides a close-up view of an inflorescence of 'Bailbudone'.

The colors in the photograph may differ slightly from the color values cited in the detailed botanical description, which accurately describe the colors of the new *Buddleia*.

DETAILED BOTANICAL DESCRIPTION

The following is a detailed description of 1.5-year-old plants of the new cultivar as grown in 2-gallon containers outdoors in Cottage Grove, Minnesota. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—June until frost in Winterville, GA.

*Plant type*.—Deciduous shrub.

*Plant habit*.—Upright rounded, compact, dense and uniform.

*Plant size*.—An average of 72 cm in height, 70 cm in spread as a 1.5-year-old plant in a container, reaches 2.4 m in height and width as a mature plant in the landscape.

*Cold hardiness*.—At least in U.S.D.A. Zone 5.

*Diseases and pests*.—No susceptibility and resistance to diseases and pests has been observed.

*Root description*.—Fibrous and fine, 160A in color.

*Propagation*.—Stem cuttings.

*Time required for root development*.—Roots initiate in an average of 15 days, a young plant is produced from a rooted cutting in an average of 40 days.

*Growth rate*.—Vigorous.

Branch description:

*Branch shape*.—Square, with raised corners down the length of the stem.

*Branch arrangement*.—Opposite, whorled.

*Branch aspect*.—Upright to outward.

*Branch color*.—Young; 145A (with flocci rubbed off), mature; 146B (with flocci rubbed off), old stems, wood; striations of 200A and 199B, and 198A.

*Branch strength*.—Strong and very flexible.

*Branch size*.—Main branch; 13 cm in length, 1.5 cm in diameter, lateral branches; 46 cm in length (excluding peduncle), 5 mm in diameter.

*Branch surface*.—Young; slightly sheen, densely covered with short, soft tangled floccose pubescence, 193A in color, mature; slightly sheen, densely covered with short, soft tangled floccose pubescence, a blend of 145A and 145C in color, old stems, wood; rugose and matte.

*Branching*.—Main stems; 1, lateral stems; 20.

*Internode length*.—5.5 cm.

Foliage description:

*Leaf shape*.—Elliptic.

*Leaf division*.—Simple.

*Leaf base*.—Cuneate.

*Leaf apex*.—Acute.

*Leaf fragrance*.—None.

*Leaf venation*.—Pinnate, colors of veins match leaf surface, main vein from mid-section to base is translucent and N144A in color.

*Leaf bulging between veins*.—Weak.

*Leaf margins*.—Serrulate.

*Leaf arrangement*.—Opposite.

*Leaf attachment*.—Sessile.

*Leaf surface*.—Young and mature upper and lower surface; matte, densely covered with minute puberulent hairs that match leaf surface color and not distinguishable.

*Leaf size*.—11.5 cm in length, 4 cm in width.

*Leaf quantity*.—An average of 18 per branch (9 pairs).

*Leaf color*.—Young and mature upper surface; NN137A, young and mature lower surface; 194A.

*Stipules*.—1 pair of 2 on each side, leaf size; 2 cm in length and 2 mm in diameter, upper surface color; NN137A, base 192A.

Inflorescence description:

*Inflorescence type*.—Compound terminal panicles roughly conical in shape.

*Inflorescence size*.—13.5 cm in height, 5 cm in diameter.

*Density of flowers within the inflorescence*.—Medium.

*Lastingness of flowers*.—An average of 9 to 12 days.

*Flower buds*.—Conical in shape, an average of 2 mm in depth and 1 mm in diameter, young buds; 4D in color, mature buds before burst; 75A in color.

*Flower aspect*.—Upright to outward.

*Flower fragrance*.—Strong and sweet.

*Flower quantity*.—Up to 1,000 flowers per inflorescence.

*Flower type*.—Single and salverform.

*Flower size*.—Average of 1 cm in depth and diameter (including tube).

*Peduncles*.—7 cm in length and 2 mm in diameter, matte and densely flocculent surface, color; 193A, with flocci rubbed off 141A.

*Pedicels*.—2 mm in length and 1 mm in diameter, matte and densely flocculent surface, color; 193A, with flocci rubbed off 141A.

*Calyx*.—Tetragonal in shape, 3 mm in depth, 1 mm in diameter.

*Sepals*.—5, fused into a campanulate overall shape, entire margins, apiculate apex, base fused, 6 mm in length and 0.75 mm in width, color; both surfaces, NN137A, base 138B, outer surface densely puberulent and matte, inner surface glabrous and glossy.

*Petals*.—4, arrangement in a single whorl and fused into narrow tube, flabellate in shape, crenate margins that are undulate, obtuse apex, an average of 4 mm in length and 3 mm in width, both surfaces are satiny sheen, glistens in the sun, color: upper surface when opening; N74B, lower surface when opening; N74C, upper surface when fully open; 68B, margins lightly flushed with 85A, center 28A, lower surface when fully open; 68B, margins lightly flushed with 85A and 49A.

*Corolla lobe attitude at full flowering*.—Horizontal.

*Corolla lobe arrangement*.—Free.

*Flower tube.*—9 mm in length, 1 mm in diameter, surfaces are slightly translucent, glabrous and matte, color: outer surface young; 37B, outer surface mature; top 38A, base 143A and 155B, inner surface young and mature; 26B.

Reproductive organs:

*Gynoecium.*—1 pistil, stigma; oblong in shape, retuse apex, fused into 2 parts, 0.5 mm in length, 16C in color, style; an average of 2 mm in length, 0.5 mm in diameter, square in shape, color; 145C, top is 144A, ovary; hypogynous, oblong and 145A in color.

*Androecium.*—Stamens; 3, filament; fused directly into center of tube, not distinguishable, anthers; minute, 0.2 mm in length, 203A in color, pollen; low, 16C in color.

*Fruit and seed.*—Have not been produced to date.

It is claimed:

1. A new and distinct cultivar of *Buddleia* plant named 'Bailbudone' as herein illustrated and described.

* * * * *